United States Patent
Andersson (10) Patent No.: US 8,116,545 B2
(45) Date of Patent: *Feb. 14, 2012

(54) METHOD AND SYSTEM FOR ANALYSIS OF BONE DENSITY

(75) Inventor: Karl-Johan Andersson, Uppsala (SE)

(73) Assignee: Crebone AB, Sundbyberg (SE)

( * ) Notice: Subject to any disclaimer, the term of this patent is extended or adjusted under 35 U.S.C. 154(b) by 0 days.

This patent is subject to a terminal disclaimer.

(21) Appl. No.: 12/853,138

(22) Filed: Aug. 9, 2010

(65) Prior Publication Data

US 2010/0322501 A1 Dec. 23, 2010

Related U.S. Application Data

(63) Continuation of application No. 11/552,998, filed on Oct. 26, 2006, now Pat. No. 7,848,551.

(51) Int. Cl.
*G06K 9/00* (2006.01)
(52) U.S. Cl. ......................... 382/128; 382/224
(58) Field of Classification Search .................. 382/128, 382/224
See application file for complete search history.

(56) References Cited

U.S. PATENT DOCUMENTS 7,848,551 B2 * 12/2010 Andersson ..................... 382/128
2008/0119719 A1 * 5/2008 Ascenzi et al. ............... 600/410

* cited by examiner

*Primary Examiner* — John Strege
(74) *Attorney, Agent, or Firm* — Clise, Billion & Cyr, P.A.; Tim Clise (57) ABSTRACT

The present description relates to a method for generating a bone density value. The method can include generating digital image data depending upon an X-ray image corresponding to at least a part of the bone; transmitting a digital image data signal comprising the digital image data; and processing said digital image data signal. The processing step can include generating a trabeculae model depending upon said processed digital image data signal; generating at least one geometrical figure depending upon the generated trabeculae model, wherein the generated geometrical figure is provided essentially within a space at least partly defined by center lines of the generated trabeculae; and calculating the bone density value depending upon the at least one generated geometrical figure. Devices and storage for the method(s) are also described.

28 Claims, 5 Drawing Sheets

METHOD AND SYSTEM FOR ANALYSIS OF BONE DENSITY

PRIORITY OF INVENTION

The present application is a continuation of U.S. application Ser. No. 11/552,998, filed Oct. 26, 2006, which is incorporated by reference for any purpose.

BACKGROUND OF THE INVENTION

Trabecular bone of mammals, for example, must withstand the loads that arise during daily activities as well as those from trauma. Investigation of the mechanical properties of trabecular bone presents a challenge because of its high porosity and complex architecture, both of which vary substantially between anatomic sites and across individuals.

Today, osteoporosis is one major cause of fragile fractures, which is a common disease in several countries. Each year immense resources of public or private medical services are used for treatment of patients suffering from bone fractures resulting from different forms of trauma. Of course, a combination of undiscovered osteoporosis and incautious activities may more easily result in bone fractures than if a diagnosis of osteoporosis would have been made and communicated.

There exist various ways to measure and/or determine bone mass and bone density. A well known procedure is to measure the density of a bone in antebrachium by means of a Dual X-ray absorptiometry (DXA). However, in practice, often a great percentage of the population in a country is vulnerable to osteoporosis but is not subjected to regular medical examinations. Use of DXA is associated with bulky equipment and high costs.

U.S. 2002 196966 discloses an automated method, storage medium, and system for analyzing bone. Digital image data corresponding to an image of the bone are obtained. Next there is determined, based on the digital images, a measure of bone mineral density (BMD) and at least one of a measure of bone geometry, a Minkowski dimension, and a trabecular orientation. The strength of the bone is estimated based upon the measure of BMD and at least one of the measure of bone geometry, the Minkowski dimension, and the trabecular orientation.

A measure of normalized bone mineral density (BMD) corresponding to a volumetric bone mineral density of the bone is determined, and the strength of the bone based is estimated based at least in part on the normalized BMD. However, the method and system is associated with a heavy computational burden.

SUMMARY

An object of the invention is to provide a more cost effective system and method for detecting an indication that a bone suffers from osteoporosis.

Yet another object of the invention is to provide a method and system which allows detecting an indication of that a bone suffers from osteoporosis in a fast, accurate and automated way, while reducing the computational complexity associated therewith.

Yet another object of the invention is to provide an improved procedure of computerized analysis of a bone, such as a jaw bone of a mammal.

Yet another object of the invention is to provide a computer program for improved computerized analysis of a bone, such as a jaw bone of a mammal.

Yet another object of the invention is to provide a method and system for generating a value indicative of bone density for a bone having at least one trabeculae.

According to an aspect of the invention there is provided a method for generating a value indicative of bone density for a bone having at least one trabeculae; said method comprising the steps of:
  generating a set of digital image data pixels depending upon an X-ray image corresponding to at least a part of said bone;
  classifying pixels selected from said set of digital image data pixels according to predefined classification rules so as to distinguish between trabeculae tissue and non-trabeculae tissue;
  processing said classified pixels so as to generate at least one trabeculae image; said at least one trabeculae image corresponding to said at least one trabeculae;
  generating at least one center line associated with said at least one trabeculae image; each said center line being indicative of a geometrical shape of said trabeculae image; and
  generating a plurality of geometrical figures; each said geometrical figure having a geometrical figure boundary defined by said center lines; said geometrical figure boundary being selected so that the area of said geometrical figure represents an area of non-trabeculae tissue located between said trabeculae.

According to an aspect of the invention the problems described above can be solved by a. method for generating a bone density value comprising the steps of:
  generating digital image data depending upon an X-ray image corresponding to at least a part of the bone;
  transmitting a digital image data signal comprising the digital image data;
  processing said digital image data signal;
wherein
said processing step comprises the sub steps of:
  generating a trabeculae model depending upon said processed digital image data signal;
  generating at least one geometrical figure depending upon the generated trabeculae model, wherein the generated geometrical figure is provided essentially within a space at least partly defined by center lines of the generated trabeculae;
  calculating the bone density value depending upon the at least one generated geometrical figure.

The method provides a low cost examination of osteoporosis presence of a mammal. This means that a relatively early detection of osteoporosis can be achieved.

Advantageously, there is achieved a reduced computational load associated with the automatic computerized analysis because of the fact that the invention is directed to determine space between trabeculae instead of performing calculations relating to the actual bone structure.

According to an aspect of the invention there is provided a computer readable medium having embodied thereon a computer program for processing by a computer comprising:
  a first code segment for processing digital image data, which data is generated depending upon an X-ray image corresponding to at least a part of a bone;
  a second code segment for generating a trabeculae model depending upon said processed digital image data;
  a third code segment for generating at least one geometrical figure depending upon the generated trabeculae model, wherein the generated geometrical figure is provided essentially within a space at least partly defined by center lines of the generated trabeculae; and a fourth code segment for calculating bone density value of the bone depending upon the at least one generated geometrical figure.

Preferably the medium is a propagated signal.

Preferably the propagated signal is a carrier wave.

According to an aspect of the invention there is provided an apparatus for generating a value indicative of bone density for a bone having at least one trabeculae; said apparatus comprising:

means for generating a set of digital image data pixels depending upon an X-ray image corresponding to at least a part of said bone;

means for classifying pixels selected from said set of digital image data pixels according to predefined classification rules so as to distinguish between trabeculae tissue and non-trabeculae tissue;

means for processing said classified pixels so as to generate at least one trabeculae image; said at least one trabeculae image corresponding to said at least one trabeculae;

means for generating at least one center line associated with said at least one trabeculae image; each said center line being indicative of a geometrical shape of said trabeculae image; and means for generating a plurality of geometrical figures; each said geometrical figure having a geometrical figure boundary defined by said center lines; said geometrical figure boundary being selected so that the area of said geometrical figure represents an area of non-trabeculae tissue located between said trabeculae.

According to an aspect of the invention there is provided a system for generating a value indicative of bone density for a bone having at least one trabeculae; said apparatus comprising:

means for generating a set of digital image data pixels depending upon an X-ray image corresponding to at least a part of said bone;

means for classifying pixels selected from said set of digital image data pixels according to predefined classification rules so as to distinguish between trabeculae tissue and non-trabeculae tissue;

means for processing said classified pixels so as to generate at least one trabeculae image; said at least one trabeculae image corresponding to said at least one trabeculae;

means for generating at least one center line associated with said at least one trabeculae image; each said center line being indicative of a geometrical shape of said trabeculae image; and means for generating a plurality of geometrical figures; each said geometrical figure having a geometrical figure boundary defined by said center lines; said geometrical figure boundary being selected so that the area of said geometrical figure represents an area of non-trabeculae tissue located between said trabeculae.

According to an aspect of the invention there is provided an apparatus for generating a bone density value, comprising:

receiving means for receiving a digital image data signal comprising digital image data generated depending upon an X-ray image corresponding to at least a part of the bone;

processing means arranged to generate a trabeculae model depending upon said processed digital image data signal; wherein the processing means further is arranged to generate at least one geometrical figure depending upon the generated trabeculae model, wherein the generated geometrical figure is provided essentially within a space at least partly defined by center lines of the generated trabeculae; and which processing means further is arranged to calculate the bone density value depending upon the at least one generated geometrical figure.

Preferably the apparatus further comprising:

means for generating a plurality of geometrical figures.

Preferably the apparatus further comprising:

means for selecting the at least one geometrical figure to be a circle.

Preferably the apparatus further comprising:

means for providing the at least one geometrical figure in a space relating to regions provided essentially between the generated trabeculae.

Preferably the apparatus further comprising:

means for manually selecting a region of interest depending upon said X-ray image, wherein at least a part of said bone is provided within said region of interest; and/or means for automatically selecting a region of interest depending upon said X-ray image, wherein at least a part of said bone is provided within said region of interest.

Preferably the apparatus further comprising:

means for normalizing said digital image data.

Preferably the apparatus further comprising:

means for generating set up information comprising information about image brightness and/or radiation dose information; and means for including the set up information in the digital image data signal.

An aspect of the invention relates to a system comprising image generating means for generating digital image data depending upon an X-ray image corresponding to at least a part of the bone;

means for transmitting a digital image data signal comprising the digital image data; and an apparatus as defined above.

According to an aspect of the invention there is provided a computer program product comprising a computer readable medium having embodied thereon a computer program for processing by a computer, said computer program comprising:

a first code segment for generating a set of digital image data pixels depending upon an X-ray image corresponding to at least a part of said bone;

a second code segment for classifying pixels selected from said set of digital image data pixels according to predefined classification rules so as to distinguish between trabeculae tissue and non-trabeculae tissue;

a third code segment for processing said classified pixels so as to generate at least one trabeculae image; said at least one trabeculae image corresponding to said at least one trabeculae;

a fourth code segment for generating at least one center line associated with said at least one trabeculae image; each said center line being indicative of a geometrical shape of said trabeculae image; and a fifth code segment for generating a plurality of geometrical figures; each said geometrical figure having a geometrical figure boundary defined by said center lines; said geometrical figure boundary being selected so that the area of said geometrical figure represents an area of non-trabeculae tissue located between said trabeculae.

Preferably the medium is a propagated signal.

Preferably said propagated signal is a carrier wave.

Additional objects, advantages and novel features of the present invention will become apparent to those skilled in the art from the following details, as well as by practice of the invention. While the invention is described below, it should be understood that the invention is not limited to the specific details disclosed. A person skilled in the art having access to the teachings herein will recognize additional applications, modifications and embodiments in other fields, which are within the scope of the invention.

BRIEF DESCRIPTION OF THE DRAWINGS

For a more complete understanding of the present invention and further objects and advantages thereof, reference is now made to the examples shown in the accompanying drawings, in which.

DETAILED DESCRIPTION OF DRAWINGS

Figure 1:
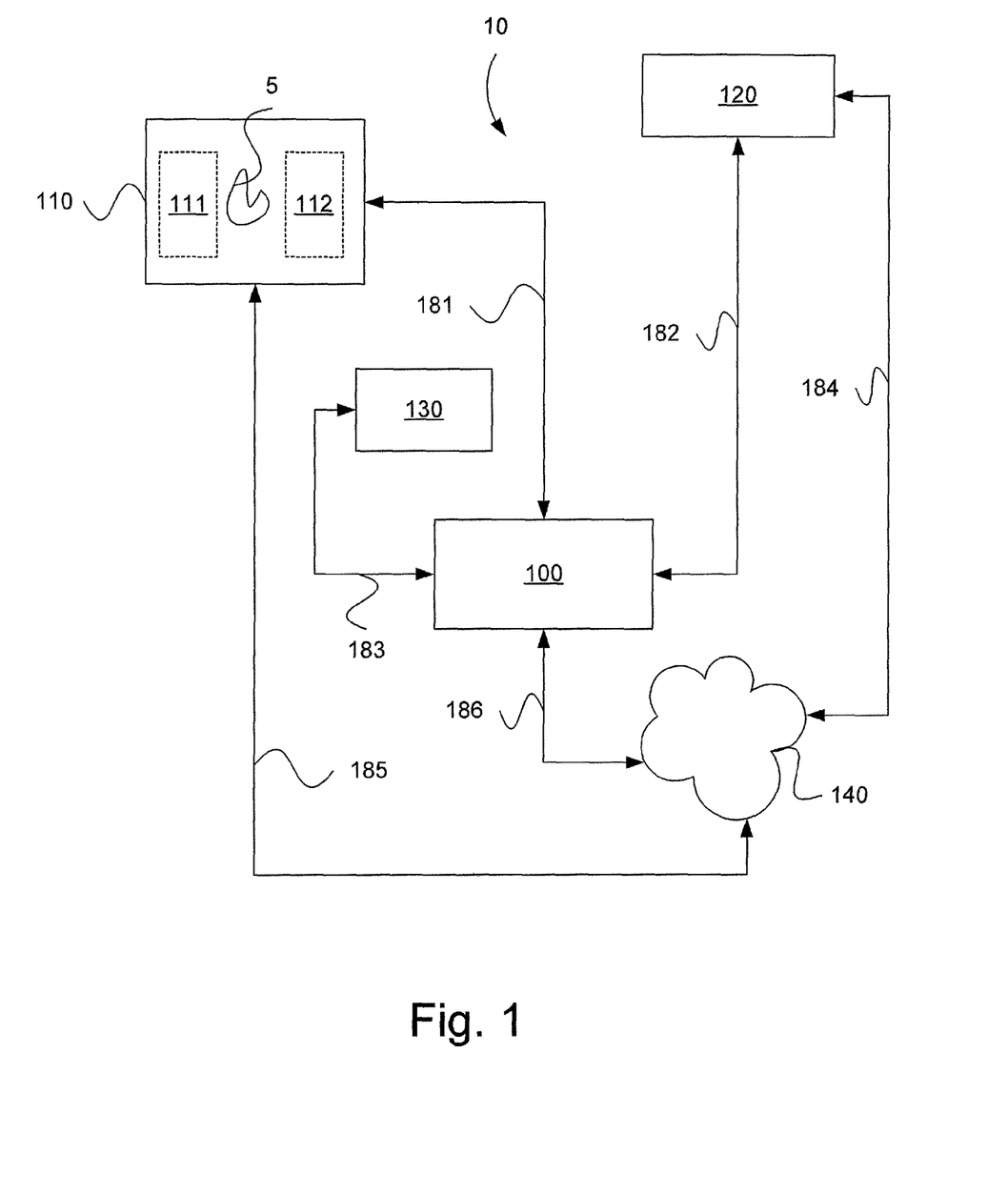
FIG. 1 schematically illustrates an overview of a system for generating bone information according to an aspect of the invention.

FIG. 1 schematically illustrates a system 10 according to an aspect of the invention. The system 10 is arranged to perform a computerized analysis of an object, such as a bone of a mammal. The system 10 is arranged for generating a piece of information comprising information about the object.

The object is referred to as object 5. According to the preferred embodiment of present invention the object is a human being. More specific, a preferred region of interest (ROI) is a mandible, i.e. a lower jaw, of a living person, such as a patient at a dentist's office. Alternatively, the object may be a bone of a dead animal to be investigated.

The system 10 comprises an image generating means 110, which is arranged for communication with an image processing means 100 via a link 181. An image providing means 120 is arranged for communication with the image processing means via a link 182. An input/output unit 130 is arranged for communication with the image processing means 100 via a link 183. The image generating means 110 and the image providing means 120 may also be arranged for communication with a communications network 140, such as a WAN, local network or Internet, via links 185 and 184, respectively. The communication network is further arranged for communication with the image processing means via a link 186.

The image generating means 110 is according to a preferred embodiment an X-ray system comprising a radiating unit 111 and a detector unit 112. The X-ray system may be of arbitrary size. The X-ray system is preferably arranged for radiating a person's jaw region, such as being performed at a dentist's office or at a hospital. The system is arranged to generate digital image data D1 corresponding to an image of a bone, for example the lower jaw bone of a person. The image generating means 110 is arranged to generate a plurality of digital image data D1-DN, where N is a positive integer.

The image generating means 110 is arranged to generate and transmit the digital image data D1-DN to the image processing means 100 via a link 181 in form of digital image data signals S1-SN, respectively. The image generating means 110 is also arranged to generate image characteristic information C1-CN, respectively, associated with each digital image data D1-DN. The image generating means 110 is arranged to incorporate image characteristic information to a corresponding image data signal S1-SN. Thus, the image data signal S1 comprises image characteristic information C1; the image data signal S2 comprises image characteristic information C2 etc.

According to an embodiment of the invention the generated image data signals S1-SN are transmitted via the network 140. This embodiment is suitable if the image generating means 110 is provided in a distanced relationship regarding the image processing means 100, for example if image processing is to be performed in a different city from where the images were generated.

According to an alternative embodiment X-ray photographs (non digital) may be transformed to digital form. This can be performed by using a suitable image providing means 120, such as a scanner. The image providing means 120 is arranged to transmit digital image data signals S1-SN, according to what is depicted with reference to the image generating means 110, and transit the signals to the image processing means 100. The image data signals S1-SN may be transmitted either via the link 182 or via the network 140, as depicted above.

The input/output unit 130 may comprise a monitor, PDA, microphone, loudspeaker, PC, or other. The input/output unit 130 may also comprise a user interface for an operator (e.g. a dentist or a medicine doctor). The input/output unit 130 is arranged to communicate a result of the computerized analysis of the object. For example by providing a representative numeric value on a screen, or by play back a voice message indicating said representative numeric value. Said value may indicate a bone hardness value, such as a bone/non-bone ratio regarding the region of interest of the object 5.

The input/output unit 130 is arranged is arranged to allow an operator to manually take part is the method according to the invention. For example, in the case of using a touch-screen as input/output unit 130, an operator may manually define the region of interest by indicating the same on said screen. Alternatively, in the case of using a monitor of a PC, the operator may manually define the region of interest by indicating the same on said monitor by means of a cursor and a mouse.

It should be noted that the term "link" herein refers to both a wireless link, such as a Bluetooth or radio link, and a physical link, such as a wire or fiber optic cable.

Figure 2:
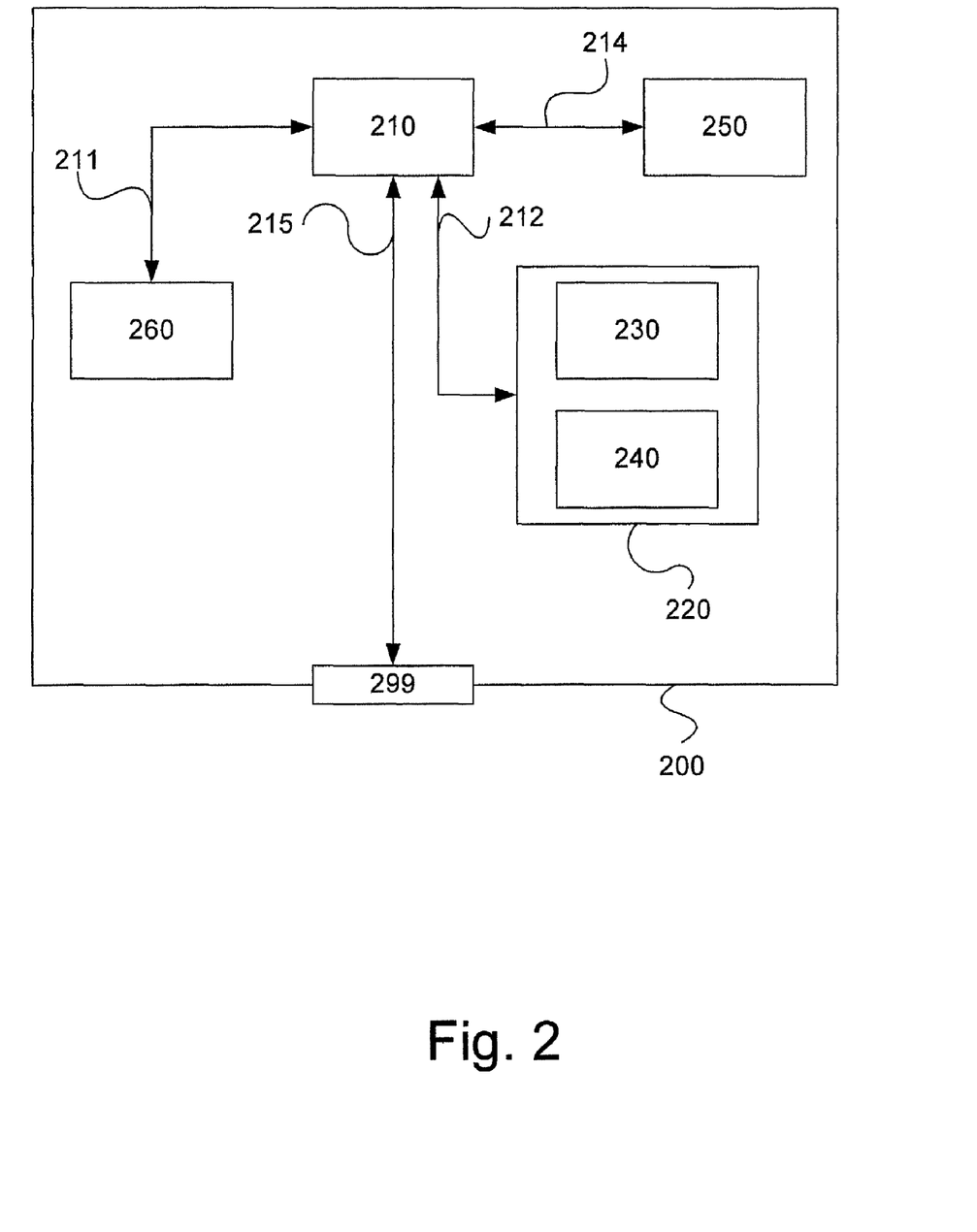
FIG. 2 schematically illustrates an arrangement according to an aspect of the present invention.

With reference to FIG. 2, a diagram of one embodiment of an apparatus 200 is shown. The above-mentioned image processing means 100 may include the apparatus 200. The apparatus 200 comprises a non-volatile memory 220, a data processing device 210 and a read/write memory 250. The non-volatile memory 220 has a first memory portion 230 wherein a computer program, such as an operating system, is stored for controlling the function of the apparatus 200. Further, the apparatus 200 comprises a bus controller, a serial communication port, I/O-means, an A/D-converter, a time date entry and transmission unit, an event counter and an interrupt controller (not shown). The non-volatile memory 220 also has a second memory portion 240.

Figure 3A:
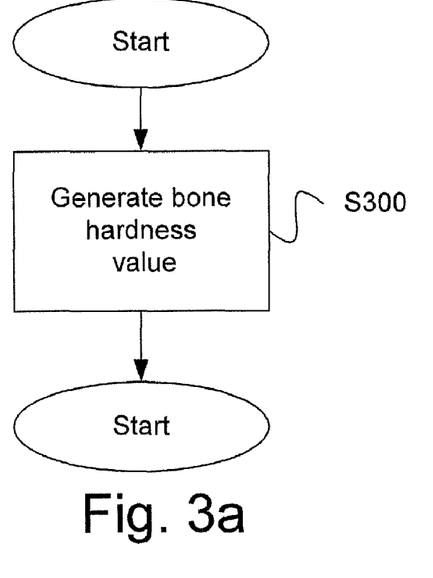
FIG. 3a schematically illustrates a method for generating bone information according to an aspect of the invention.
Figure 3B:
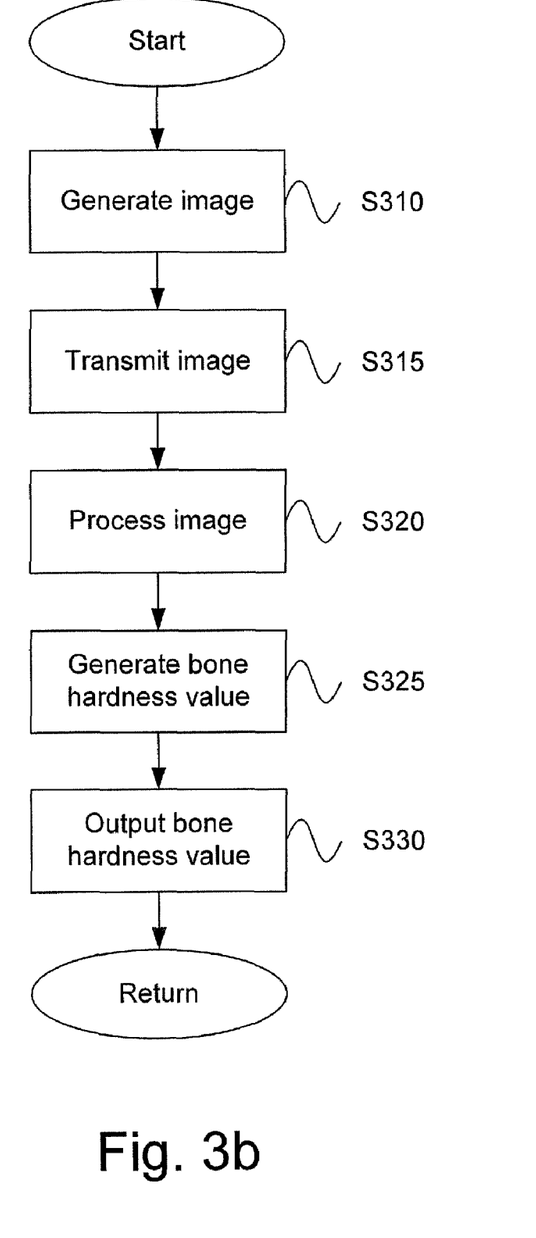
FIG. 3b schematically illustrates a method for generating bone information in greater detail according to an aspect of the invention.
Figure 3C:
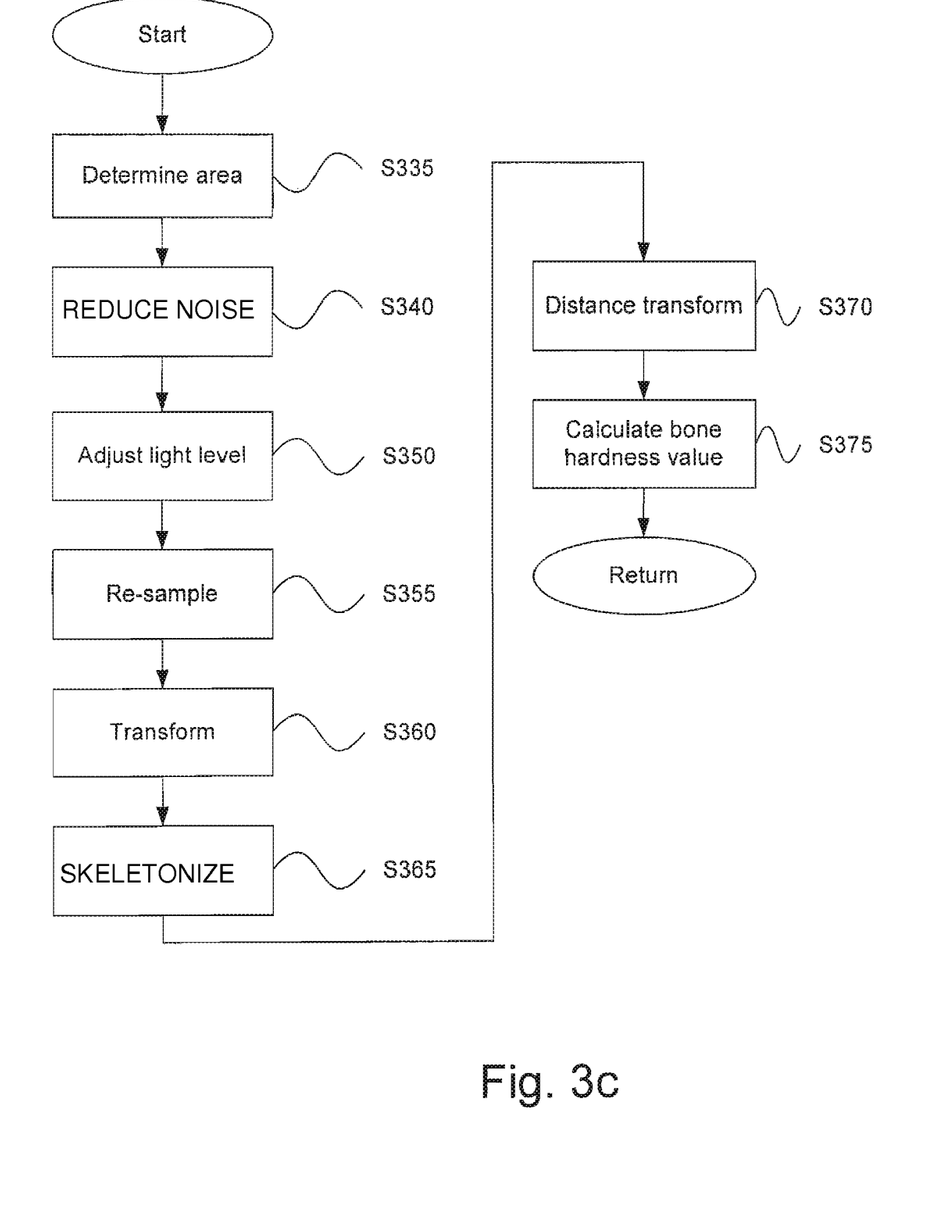
FIG. 3c schematically illustrates a method for generating bone information in greater detail according to an aspect of the invention.

A computer program comprising routines for carrying out processing and analysis of the image data signals S1-SN and further implementing predetermined actions, such as generating an indication of presence of Osteoporosis is provided. The program may be stored in an executable manner or in a compressed state in a memory 260 and/or in read/write memory 250. At least one computer program arranged to perform method steps according to FIG. 3a-3c is provided in either the memory 260 and/or in read/write memory 250.

The data processing device 200 may be, for example, a microprocessor.

When it is described that the data processing device 210 performs a certain function it should be understood that the data processing device 210 performs a certain part of the programs which are stored in the memory 260, or a certain part of the program which is stored in the read/write memory 250.

The data processing device 210 may communicate with a data port 290 by means of a data bus 215. The non-volatile memory 220 is adapted for communication with the data processing device 210 via a data bus 212. The separate memory 260 is adapted to communicate with the data processing device 210 via data bus 211. The read/write memory 250 is adapted to communicate with the data processing device 210 via a data bus 214.

When data, such as data provided in the signals S1-SN, is received on the data port 290 it is temporarily stored in the second memory portion 240. When the received input data has been temporarily stored, the data processing device 210 is set up to perform execution of code in a manner described above. According to one embodiment, data received on the data port 290 comprises information about at least one digital image corresponding to an object, wherein a region of interest (ROI) is selected. This information can be used by the apparatus 200 so as to generate an accurate indication of to what extent, if at all, a person suffers from Osteoporosis.

Parts of the methods described herein can be performed by the apparatus 200 by means of the data processing device 210 running the program stored in the memory 260 or read/write memory 250. When the apparatus 200 runs the program, parts of herein described methods are executed.

FIG. 3a schematically illustrates a method for generating a bone hardness value according to an aspect of the invention.

The method comprises a method step S300 regarding a method for generating a bone density value.

The method step S300 comprising the sub steps of:
generating digital image data depending upon an X-ray image corresponding to at least a part of the bone;
transmitting a digital image data signal comprising the digital image data;
processing said digital image data signal;
wherein
said processing step comprises the sub steps of:
generating a trabeculae model depending upon said processed digital image data signal;
generating at least one geometrical figure depending upon the generated trabeculae model, wherein the generated geometrical figure is provided essentially within a space at least partly defined by center lines of the generated trabeculae;
calculating the bone density value depending upon the at least one generated geometrical figure.
Preferably the method further comprises the step of generating a plurality of geometrical figures.
Preferably the method further comprises the step of:
selecting the at least one geometrical figure to be a circle.
Preferably the method further comprises the step of:
providing the at least one geometrical figure in a space relating to regions provided essentially between the generated trabeculae.
Preferably the method further comprises the step of:
manually selecting a region of interest depending upon said X-ray image, wherein at least a part of said bone is provided within said region of interest; or
automatically selecting a region of interest depending upon said X-ray image, wherein at least a part of said bone is provided within said region of interest.
Preferably the method further comprises the step of:
normalizing said digital image data.
Preferably the method further comprises the steps of:
generating set up information comprising information about image brightness and/or radiation dose information; and
including the set up information in the digital image data signal.

FIG. 3b schematically illustrates a method for generating a bone hardness value in greater detail according to an aspect of the invention.

The method comprises a first method step S310. The method step S310 comprises a sub step of generating digital image data corresponding to at least one image of an object 5 based upon detected X-rays. According to a preferred embodiment the generated X-ray image comprises information relating to a jaw bone of a mammal, such as a human being. Next, a subsequent method step S315 is performed.

The method step S310 comprises a step of transmitting digital image data (D1-DN) relating to the at least one digital image as a corresponding signal (S1-SN). Image set up parameters are also included. Typical parameters are image resolution information and image radiation dose information. Next, a subsequent method step S320 is performed.

The method step S320 comprises a step of processing the received digital image signals S1-SN relating to the at least one digital image, respectively. This step is depicted in greater detail with reference to FIG. 3c. Next, a subsequent method step S325 is performed.

The method step S320 comprises a step of generating a bone hardness value depending upon said processing of the received digital image signals S1-SN relating to the at least one digital image, respectively. Next, a subsequent method step S330 is performed.

The method step S320 comprises a step of outputting the generated bone structure strength value. The value can for example be displayed on a monitor or provided by means of a loudspeaker. Thereafter the method ends.

With reference to FIG. 3c a part of a method for generating a bone hardness value is depicted in greater detail according to an embodiment of the invention.

The method comprises a first method step S335. The method step S335 comprises a step of determining a region of interest (ROI) of least one image in digital form based upon detected X-rays. This method step could be performed manually or automatically as depicted with reference to FIG. 1. If the method step is performed automatically a manual check may be arbitrary performed. Next, a subsequent method step S340 is performed.

The method step S340 comprises a step of reducing noise of the at least one image. This noise may be a result of different sources. For example, one noise source is the detector unit 112 arranged to receive X-rays propagated through at least a part of the object 5, such as a lower jaw bone of a person, within an X-ray apparatus 110. The noise reduction process may be performed by known methods, such as, median filtering or in combination with linear convolution based methods. Next, a subsequent method step S350 is to be performed.

The method step S350 comprises a step of adjusting brightness of the at least one image. This step is performed using various known methods based on intensity histogram analysis. Next, a subsequent method step S355 is to be performed.

The method step S355 comprises a step of re-sampling the digital image data of the signals S1-SN relating to the at least one digital image, respectively. According to an embodiment of the invention, a down-sampling of the data is performed providing a lower resolution of the images. Next, a subsequent method step S360 is to be performed.

It should be noted that the method steps depicted above with particular reference to S340, S350 and S355 relate to a procedure of normalizing the digital image data corresponding to the at least one image. This may of course be performed in various ways. However, for the sake of clarity only these steps are depicted. A person skilled in the art would be able to modify the depicted normalization process according to specific needs. One purpose of normalizing the digital image data is to achieve a set of data having desired properties for further processing. The normalized set of digital image data relating to a specific generated image is comparable with other normalized digital image data relating to another specific generated image, regarding for example image resolution and radiation dose. It should however be noted that other set up parameters may be of relevance in a normalization process. Examples of such parameters are exposure time, bit depth/intensity quantization, X-ray acquisition method.

The method step S360 comprises a step of transforming the normalized digital image intensity data to binary data form. According to an aspect of the invention the set of data is transformed to tertiary data. According to an aspect of the invention the set of data is transformed to an arbitrary degree of differentiation, for example a fourth or fifth degree of differentiation. Next, a subsequent method step S365 is to be performed.

Thus a classification process of normalized digital image data relating to each pixel thereof is performed. This process may comprise the sub steps of comparing digital image data associated with each pixel of the image with digital image data associated with each adjacent pixel. For example, each pixel of the image could be compared with the eight closest pixels regarding for example brightness. If the brightness of an adjacent pixel is larger than a predetermined threshold value the two pixels is classified as belonging to different components of the object, for example, jaw bone and gums.

When all pixels have been classified, regarding for example brightness, a filtering process is applied. This filtering process involves different aspects of changing classification of individual pixels of the image as well as set of pixels. For example, if one pixel in a center of a large group of pixels is deviating regarding its classification this pixel may be re-classified, in accordance with the surrounding pixels. The same principles may apply to a group of deviating pixels within a particular area of the region of interest. There exist standard methods for performing a filtering process according to what is generally depicted above. Examples of such mathematical morphology methods are opening, closing, thinning and pruning.

The method step S365 comprises a step of performing a skeletonizing process. Standard techniques are available on the market today. In short, skeletonization is basically a process for reducing foreground regions in a binary image to a skeletal remnant that largely preserves the extent and connectivity of the original region while reducing most of the original foreground pixels.

Herein, one or more center axes are generated and associated with each generated trabeculae. This is depicted in greater detail with reference to FIG. 5b. Next, a subsequent method step S370 is to be performed.

The method step S370 comprises a step of performing a distance transformation on the area between the skeletonized trabeculae. The step of distance transformation is performed depending upon the generated skeleton model with reference to the method step S365. One way to perform this step is to determine, for each pixel of the digital image, distances from a pixel to a closest pixel which is provided at a center axis, i.e. for each pixel of the image the shortest distance to a skeleton pixel is determined.

According to a preferred embodiment circles are generated depending upon said distance transformation. However, an arbitrary geometrical figure may be used, for example hexagons or heptagons. The number and the size of geometrical figures within the selected region of interest is a measure of trabeculae density of the bone. This measure is an indication of how many trabeculae there is provided within the region of interest. Studies have shown that this value, which according to a preferred embodiment is associated with a lower jaw bone of a person is indicative of the number of trabeculae in a region located in a different bone of the person's body, for example an upper end (at a hip) of femur.

There is an advantage associated with this procedure because it is less depending upon faulty segmentation of the trabeculae.

Next, a method step S375 is performed. The method step S375 comprises the step of calculating a numerical value indicating how much space there is between the generated trabeculae. This calculation is performed depending upon the number of generated geometric figures within the region of interest. This calculation is performed depending upon the size of the generated geometric figures. Preferably the geometric figures are circles. In the case of the geometric figures are circles, their respective radius is taken into account in the calculation. The calculated numerical value may be an indication of bone density. The calculated numerical value is then outputted. Alternatively, a symbol representing the numerical value is outputted.

An aspect of the invention relates to a computer program comprising a program code for performing the method steps according to the invention, when the computer program is run on a computer.

An aspect of the invention relates to a computer program product comprising a program code stored on computer-readable media for performing the method steps according to the invention, when the computer program is run on the computer.

An aspect of the invention relates to a computer program product directly storable in an internal memory of a computer, comprising a computer program for performing the method steps according to the invention, when the computer program is run on the computer.

Figure 4:
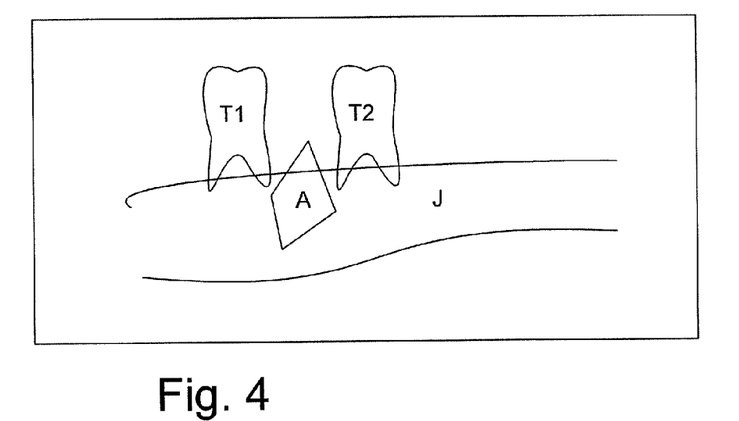
FIG. 4 schematically illustrates a representation of an X-ray image.

FIG. 4 schematically illustrates a simplified representation of a 2-D digital image generated depending upon detected X-rays transmitted through an object. According to a preferred embodiment the object is a part of a mammal or other type of animal comprising an internal skeleton. According to more preferred embodiment of the invention the object is a part of a mammal, wherein said object comprises at least a part of a bone, preferably trabecular bone. According to a preferred embodiment the object is a part of a mammal's head, such as a jaw bone.

The invention is advantageous because digital X-ray generated image data may be produced in a situation where a patient is visiting a dentist. It should be noted that this typically generated digital image data is well suited for being processed according to the invention.

The digital image data indicates that the object which has been subjected to X-rays by the image generating means is a part comprising two teeth and a lower jaw bone. There is indicated that an automatically or manually selected region of interest A is located essentially covering a part of the jaw bone and to a small extent gums between the first and second tooth T1 and T2. The region of interest is also referred to as ROI.

Figure 5A:
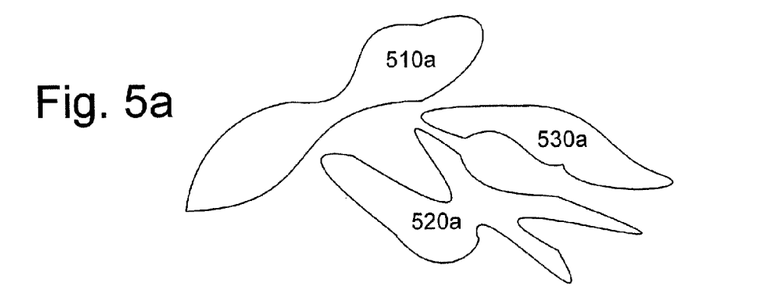
FIG. 5a schematically illustrates a set of trabeculae generated by a skeletonization process.

FIG. 5a schematically illustrates a skeleton model regarding a selected region of interest A. This skeleton model comprises three separated trabeculae 510a, 520a and 530a, respectively. It should be noted that only a 2-D model is depicted with reference to the FIGS. 5a-5c.

The trabeculae 510a, 520a and 530a has been generated by means of a skeletonizing procedure. The trabeculae 510a is referred to as a first trabeculae 510a. The trabeculae 520a is referred to as a second trabeculae 520a. The trabeculae 530a is referred to as a third trabeculae 530a. The trabeculae 510a, 520a and 530a thus represent three trabeculae which are automatically identified from the digital image data, for example D1.

Figure 5B:
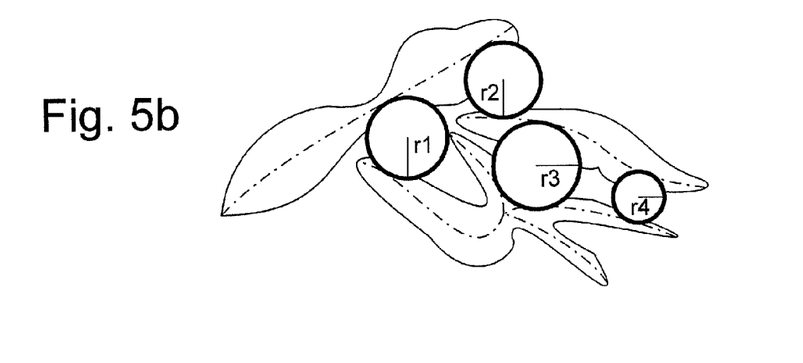
FIG. 5b schematically illustrates the set of trabeculae provided with center lines.

FIG. 5b schematically illustrates an example of generated center lines. The first trabeculae 510a is provided with a first center axis 510b. The second trabeculae 520a is provided with four center axes 520b1, 520b2, 520b3 and 520b4, respectively. Depending upon the shape of a particular trabeculae an arbitrary number of center axes may be generated. The third trabeculae 530a is provided with a first center axis 530b. Further, two pixel points P1 and P2 are illustrated.

Figure 5C:
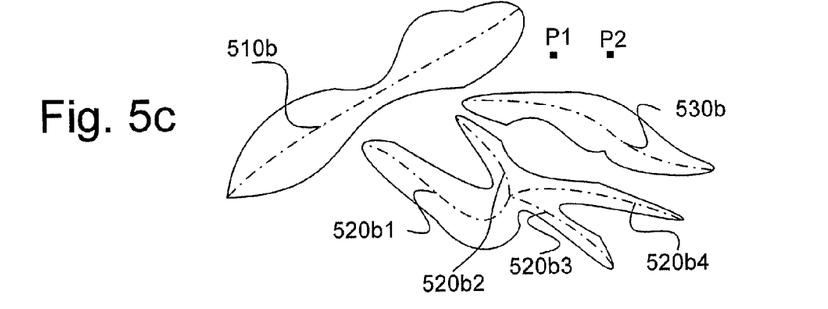
FIG. 5c schematically illustrates the set of trabeculae provided with geometrical figures.

FIG. 5c schematically illustrates four generated example circles of different radius r1, r2, r3 and r4. As can be seen they are all fitted between the generated center axes of the generated trabeculae. These circles are automatically analyzed so as to generate a bone density value or a value indicating to what extent the bone of the object suffers from Osteoporosis.

The foregoing description of the preferred embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated.

The invention claimed is:

1. A system for generating a bone density value, comprising
a transmitter to transmit a digital image data signal including digital image data representing a bone image; and
a receiver to receive the digital image data signal including digital image data generated from an X-ray image corresponding to at least a part of the bone;
one or more processors to generate a trabeculae model from the processed digital image data signal; wherein the one or more processors generate geometrical figures from the generated trabeculae model from selected pixels of the digital image data signal, and wherein a first generated geometrical figure is provided substantially within a space at least partly defined by center lines of the generated trabeculae and a second geometrical figure including a boundary being selected so that the area of the geometrical figure represents an area of non-trabeculae tissue located between the trabeculae; and the one or more processors calculate the bone density value from the at least one generated geometrical figure.

2. The apparatus of claim 1, further comprising a generator to generate a plurality of geometrical figures.

3. The apparatus of claim 1, further comprising one or more processors to select the at least one geometrical figure to be a circle.

4. The apparatus of claim 1, wherein the at least one geometrical figure is found in a space relating to regions provided substantially between the generated trabeculae.

5. The apparatus of claim 1, further comprising a selection module to manually select a region of interest from the X-ray image, wherein at least a part of the bone is provided within the region of interest.

6. The apparatus of claim 1, further comprising a processor to normalize the digital image data.

7. The apparatus of claim 1, further comprising a processor to generate set up information including information about image brightness, radiation dose information or both, and a processor to include the set up information in the digital image data signal.

8. The apparatus of claim 1, comprising an image generator to generate the digital image from at least a part of a bone.

9. An apparatus for generating a value indicative of bone density for a bone having at least one trabeculae comprising:
a processor to classify pixels selected from a set of digital image data pixels according to predefined classification rules so as to distinguish between trabeculae tissue and non-trabeculae tissue;
a processor to select the classified pixels so as to generate at least one trabeculae image; the at least one trabeculae image corresponding to the at least one trabeculae;
a generator to generate at least one center line associated with the at least one trabeculae image; each center line being indicative of a geometrical shape of the trabeculae image; and
a generator to generate a plurality of geometrical figures; each geometrical figure including a geometrical figure boundary defined by the center lines; the geometrical figure boundary being selected so that the area of the geometrical figure represents an area of non-trabeculae tissue located between the trabeculae.

10. The apparatus of claim 9, comprising an image generator to generate the set of digital image data pixels from an X-ray image corresponding to at least a part of a bone.

11. A system for generating a value indicative of bone density for a bone having at least one trabeculae comprising:
a processor to classify pixels selected from a set of digital image data pixels according to predefined classification rules so as to distinguish between trabeculae tissue and non-trabeculae tissue;
a processor to select the classified pixels so as to generate at least one trabeculae image; the at least one trabeculae image corresponding to the at least one trabeculae;
a generator to generate at least one center line associated with the at least one trabeculae image; each center line being indicative of a geometrical shape of the trabeculae image; and
a generator to generate a plurality of geometrical figures; each geometrical figure including a geometrical figure boundary defined by the center lines; the geometrical figure boundary being selected so that the area of the geometrical figure represents an area of non-trabeculae tissue located between the trabeculae.

12. The system of claim 11 comprising an image generator to generate a set of digital image data pixels from an X-ray image corresponding to at least a part of a bone.

13. A non-transitory computer readable medium storing instructions, which are executable by a computer, the instructions comprising:
classifying pixels selected from said set of digital image data pixels according to predefined classification rules so as to distinguish between trabeculae tissue and non-trabeculae tissue;
processing said classified pixels so as to generate at least one trabeculae image; said at least one trabeculae image corresponding to said at least one trabeculae;
generating at least one center line associated with said at least one trabeculae image; each said center line being indicative of a geometrical shape of said trabeculae image; and
generating a plurality of geometrical figures; said geometrical figure including a geometrical figure boundary defined by said center lines; said geometrical figure boundary being selected so that the area of said geometrical figure represents an area of non-trabeculae tissue located between said trabeculae.

14. The computer readable medium of claim 13, wherein the instructions comprise generating the set of digital image data pixels using an X-ray image corresponding to at least a part of said bone.

15. The computer readable medium of claim 13, wherein the instructions comprise setting up image brightness, radiation dose information or both, and including the set up information in the digital image data signal.

16. The computer readable medium of claim 13, wherein the instructions comprise generating a plurality of geometrical figures.

17. The computer readable medium of claim 16, wherein the instructions comprise selecting the at least one geometrical figure to be a circle.

18. The computer readable medium of claim 17, wherein the instructions comprise positioning the at least one geometrical figure in a space relating to regions provided between the generated trabeculae.

19. The computer readable medium of claim 18, wherein at least one of the instructions are stored on internal computer memory.

20. The computer readable medium of claim 13, comprising instructions to automatically select a region of interest from the X-ray image, wherein at least a part of the bone is provided within the region of interest.

21. A method for generating a value indicative of bone density for a bone having at least one trabeculae comprising:
classifying pixels selected from said set of digital image data pixels according to predefined classification rules so as to distinguish between trabeculae tissue and non-trabeculae tissue;
processing said classified pixels so as to generate at least one trabeculae image; said at least one trabeculae image corresponding to said at least one trabeculae;
generating at least one center line associated with said at least one trabeculae image; each said center line being indicative of a geometrical shape of said trabeculae image; and
generating a plurality of geometrical figures; said geometrical figure including a geometrical figure boundary defined by said center lines; said geometrical figure boundary being selected so that the area of said geometrical figure represents an area of non-trabeculae tissue located between said trabeculae.

22. The method of claim 21, further comprising generating the set of digital image data pixels using an X-ray image corresponding to at least a part of said bone.

23. The method of claim 21, further comprising setting up image brightness, radiation dose information or both, and including the set up information in the digital image data signal.

24. The method of claim 21, further comprising generating a plurality of geometrical figures.

25. The method of claim 21, further comprising selecting the at least one geometrical figure to be a circle.

26. The method of claim 21, further comprising positioning the at least one geometrical figure in a space relating to regions provided between the generated trabeculae.

27. The method of claim 21, further comprising automatically selecting a region of interest from the X-ray image, wherein at least a part of the bone is provided within the region of interest.

28. The method of claim 21, further comprising transmitting a digital image data signal including digital image data of at least part of a bone.

\* \* \* \* \*